US009439866B2

(12) United States Patent
Gervais et al.

(10) Patent No.: US 9,439,866 B2
(45) Date of Patent: *Sep. 13, 2016

(54) TRAZODONE COMPOSITION FOR ONCE A DAY ADMINISTRATION

(75) Inventors: Sonia Gervais, Laval (CA); Damon Smith, Saint-Laurent (CA); Miloud Rahmouni, Pierrefonds (CA); Pauline Contamin, Magny en Vexin (FR); Rachid Ouzerourou, Anjou (CA); My Linh Ma, Saint-Laurent (CA); Angela Ferrada, Montreal (CA); Fouzia Soulhi, Dollard-des-Ormeaux (CA)

(73) Assignee: Angelini Pharma, Inc., Gaithersburg, MD (US)

( * ) Notice: Subject to any disclaimer, the term of this patent is extended or adjusted under 35 U.S.C. 154(b) by 999 days.

This patent is subject to a terminal disclaimer.

(21) Appl. No.: 12/892,454

(22) Filed: Sep. 28, 2010

(65) Prior Publication Data

US 2011/0021535 A1  Jan. 27, 2011

Related U.S. Application Data

(63) Continuation of application No. 11/519,194, filed on Sep. 11, 2006, now Pat. No. 7,829,120.

(60) Provisional application No. 60/715,162, filed on Sep. 9, 2005.

(51) Int. Cl.

| A61K 9/20 | (2006.01) |
|---|---|
| A61K 9/28 | (2006.01) |
| A61K 31/16 | (2006.01) |
| A61K 31/496 | (2006.01) |
| A61K 31/135 | (2006.01) |
| A61K 31/167 | (2006.01) |
| A61K 31/4402 | (2006.01) |

(52) U.S. Cl.
CPC ............. *A61K 9/2072* (2013.01); *A61K 9/205* (2013.01); *A61K 9/2054* (2013.01); *A61K 9/2059* (2013.01); *A61K 9/28* (2013.01); *A61K 9/2866* (2013.01); *A61K 31/135* (2013.01); *A61K 31/16* (2013.01); *A61K 31/167* (2013.01); *A61K 31/4402* (2013.01); *A61K 31/496* (2013.01)

(58) Field of Classification Search
None
See application file for complete search history.

(56) References Cited

U.S. PATENT DOCUMENTS

| 2,987,445 A | 6/1961 | Levesque |
|---|---|---|
| 3,087,860 A | 4/1963 | Endicott et al. |
| 3,336,200 A | 8/1967 | Krause et al. |
| 3,381,009 A | 4/1968 | Palazzo et al. |
| 3,652,589 A | 3/1972 | Flick et al. |
| 4,131,675 A | 12/1978 | Silvestrini |
| 4,353,887 A | 10/1982 | Hess et al. |
| 4,465,660 A | 8/1984 | David et al. |
| 4,547,359 A | 10/1985 | Zierenberg et al. |
| 4,595,587 A | 6/1986 | Zierenberg et al. |
| 4,683,131 A | 7/1987 | Zierenberg et al. |
| 4,820,522 A | 4/1989 | Radebaugh et al. |
| 4,824,677 A | 4/1989 | Shah et al. |
| 4,906,632 A | 3/1990 | Silvestrini et al. |
| 4,938,968 A | 7/1990 | Mehta |
| 4,968,509 A | 11/1990 | Radebaugh et al. |
| 5,004,613 A | 4/1991 | Radebaugh et al. |
| 5,126,145 A | 6/1992 | Evenstad et al. |
| 5,132,116 A | 7/1992 | Sournac et al. |
| 5,133,974 A | 7/1992 | Paradissis et al. |
| 5,273,760 A | 12/1993 | Oshlack et al. |
| 5,286,493 A | 2/1994 | Oshlack et al. |
| 5,336,691 A | 8/1994 | Raffa et al. |
| 5,407,686 A | 4/1995 | Patel et al. |
| 5,414,129 A | 5/1995 | Cherkez et al. |
| 5,427,799 A | 6/1995 | Valentine et al. |
| 5,451,409 A | 9/1995 | Rencher et al. |
| 5,456,921 A | 10/1995 | Mateescu et al. |
| 5,478,577 A | 12/1995 | Sackler et al. |
| 5,520,931 A | 5/1996 | Persson et al. |
| 5,560,331 A | 10/1996 | Komatsu et al. |
| 5,562,924 A | 10/1996 | Perrier et al. |
| 5,580,578 A | 12/1996 | Oshlack et al. |
| 5,591,452 A | 1/1997 | Miller et al. |

(Continued)

FOREIGN PATENT DOCUMENTS

| CA | 970688 | 7/1975 |
|---|---|---|
| CA | 2 140 032 | 2/1994 |

(Continued)

OTHER PUBLICATIONS

Brooks et al., "Trazodone—A Comparison of Single Night-time and Divided Daily Dosage Regimens," Psychopharmacology 84:1-4 (1984).

(Continued)

*Primary Examiner* — Susan Tran

(74) *Attorney, Agent, or Firm* — Goodwin Procter LLP

(57) ABSTRACT

The invention relates to a once a day formulation of trazodone or a trazodone derivative. The formulation contains trazodone or a trazodone derivative and a controlled release excipient so that, once administered orally, the trazodone or the trazodone derivative is maintained at a therapeutic plasma concentration from at least 1 hour to at least 24 hours after initial administration. After administration, the initial therapeutic action takes effect within the first hour and lasts at least about 24 hours. This therapeutic effect remains relatively and substantially stable for the remaining period of 24 hours. The formulations can be used for treating depression and/or sleeping disorders.

15 Claims, 3 Drawing Sheets

(56) References Cited

U.S. PATENT DOCUMENTS

| | | |
|---|---|---|
| 5,595,762 A | 1/1997 | Derrieu et al. |
| 5,601,842 A | 2/1997 | Bartholomaeus et al. |
| 5,603,956 A | 2/1997 | Mateescu et al. |
| 5,616,343 A | 4/1997 | Cartilier et al. |
| 5,639,476 A | 6/1997 | Oshlack et al. |
| 5,663,279 A | 9/1997 | Kuiper et al. |
| 5,672,360 A | 9/1997 | Sackler et al. |
| 5,672,755 A | 9/1997 | Lerman et al. |
| 5,681,585 A | 10/1997 | Oshlack et al. |
| 5,773,031 A | 6/1998 | Shah et al. |
| 5,776,492 A | 7/1998 | Betzing et al. |
| 5,780,057 A | 7/1998 | Conte et al. |
| 5,807,575 A | 9/1998 | Dumoulin et al. |
| 5,814,338 A | 9/1998 | Veronesi et al. |
| 5,843,480 A | 12/1998 | Miller et al. |
| 5,849,240 A | 12/1998 | Miller et al. |
| 5,874,620 A | 2/1999 | Lerman et al. |
| 5,877,351 A | 3/1999 | Anderson |
| 5,879,705 A | 3/1999 | Heafield et al. |
| 5,879,707 A | 3/1999 | Cartilier et al. |
| 5,885,615 A | 3/1999 | Chouinard et al. |
| 5,888,545 A | 3/1999 | Landgraf et al. |
| 5,891,471 A | 4/1999 | Miller et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 5,981,592 A | 11/1999 | Wechter et al. |
| 6,077,537 A | 6/2000 | Booth et al. |
| 6,103,261 A | 8/2000 | Chasin et al. |
| 6,120,803 A | 9/2000 | Wong et al. |
| 6,129,205 A | 10/2000 | Ergenbright et al. |
| 6,129,933 A | 10/2000 | Oshlack et al. |
| 6,143,322 A | 11/2000 | Sackler et al. |
| 6,143,325 A | 11/2000 | Dennis et al. |
| 6,143,328 A | 11/2000 | Heafield et al. |
| 6,143,353 A | 11/2000 | Oshlack et al. |
| 6,156,342 A | 12/2000 | Sriwongjanya et al. |
| 6,156,343 A * | 12/2000 | Morita et al. ............... 424/474 |
| 6,162,467 A | 12/2000 | Miller et al. |
| 6,190,591 B1 | 2/2001 | van Lengerich |
| 6,210,714 B1 | 4/2001 | Oshlack et al. |
| 6,211,229 B1 | 4/2001 | Kavey |
| 6,214,331 B1 | 4/2001 | Vanderhoff et al. |
| 6,228,875 B1 | 5/2001 | Tsai et al. |
| 6,238,698 B1 | 5/2001 | Cremer et al. |
| 6,245,356 B1 | 6/2001 | Baichwal |
| 6,245,357 B1 | 6/2001 | Edgren et al. |
| 6,245,387 B1 | 6/2001 | Hayden |
| 6,248,363 B1 | 6/2001 | Patel et al. |
| 6,254,881 B1 | 7/2001 | McNally et al. |
| 6,254,887 B1 | 7/2001 | Miller et al. |
| 6,261,599 B1 | 7/2001 | Oshlack et al. |
| 6,277,887 B1 | 8/2001 | Young |
| 6,284,273 B1 | 9/2001 | Lenaerts et al. |
| 6,287,599 B1 | 9/2001 | Burnside et al. |
| 6,294,195 B1 | 9/2001 | Oshlack et al. |
| 6,306,438 B1 | 10/2001 | Oshlack et al. |
| 6,316,031 B1 | 11/2001 | Oshlack et al. |
| 6,326,027 B1 | 12/2001 | Miller et al. |
| 6,326,404 B1 | 12/2001 | Koegel et al. |
| 6,335,033 B2 | 1/2002 | Oshlack et al. |
| 6,339,105 B1 | 1/2002 | Kamin et al. |
| 6,372,255 B1 | 4/2002 | Saslawski et al. |
| 6,387,404 B2 | 5/2002 | Oshlack et al. |
| 6,399,096 B1 | 6/2002 | Miller et al. |
| 6,419,957 B1 | 7/2002 | Lenaerts et al. |
| 6,451,350 B1 | 9/2002 | Bartholomaeus et al. |
| 6,498,196 B1 * | 12/2002 | Roberts et al. ............... 514/712 |
| 6,558,701 B2 | 5/2003 | Bartholomaeus et al. |
| 6,569,463 B2 | 5/2003 | Patel et al. |
| 6,572,885 B2 | 6/2003 | Oshlack et al. |
| 6,576,260 B2 | 6/2003 | Bartholomaeus et al. |
| 6,586,006 B2 | 7/2003 | Roser et al. |
| 6,593,373 B2 | 7/2003 | Koegel et al. |
| 6,607,748 B1 | 8/2003 | Lenaerts et al. |
| 6,632,640 B1 | 10/2003 | Lee et al. |
| 6,635,279 B2 | 10/2003 | Kolter et al. |
| 6,645,537 B2 | 11/2003 | Sweeney et al. |
| 6,659,373 B1 | 12/2003 | Heren et al. |
| 6,660,774 B2 | 12/2003 | Christoph et al. |
| 6,685,964 B1 | 2/2004 | Bartholomaeus et al. |
| 6,723,343 B2 | 4/2004 | Kugelmann |
| 6,733,783 B2 | 5/2004 | Oshlack et al. |
| 6,743,442 B2 | 6/2004 | Oshlack et al. |
| 6,806,293 B1 | 10/2004 | Zamir et al. |
| 6,806,294 B2 | 10/2004 | Wimmer et al. |
| 6,863,901 B2 | 3/2005 | Hirsh et al. |
| 6,923,988 B2 | 8/2005 | Patel et al. |
| 6,962,717 B1 | 11/2005 | Huber et al. |
| 6,968,551 B2 | 11/2005 | Hediger et al. |
| 7,074,430 B2 | 7/2006 | Miller et al. |
| RE39,221 E | 8/2006 | Raffa et al. |
| 7,083,807 B2 | 8/2006 | Fanara et al. |
| 7,413,749 B2 | 8/2008 | Wright et al. |
| 7,829,120 B2 * | 11/2010 | Gervais et al. ............... 424/489 |
| 7,988,998 B2 | 8/2011 | Lenaerts et al. |
| 2001/0019725 A1 | 9/2001 | Miller et al. |
| 2001/0036477 A1 | 11/2001 | Miller et al. |
| 2001/0038852 A1 | 11/2001 | Kolter et al. |
| 2002/0008133 A1 | 1/2002 | Imasaki et al. |
| 2002/0012701 A1 | 1/2002 | Kolter et al. |
| 2002/0032239 A1 | 3/2002 | Koegel et al. |
| 2002/0044966 A1 | 4/2002 | Bartholomaeus et al. |
| 2002/0052411 A1 | 5/2002 | Gobel et al. |
| 2002/0055544 A1 | 5/2002 | Kamin et al. |
| 2002/0106408 A1 | 8/2002 | Bacon et al. |
| 2002/0165246 A1 | 11/2002 | Holman |
| 2002/0176888 A1 | 11/2002 | Bartholomaeus et al. |
| 2003/0021846 A1 | 1/2003 | Kolter et al. |
| 2003/0035835 A1 | 2/2003 | Bartholomaeus et al. |
| 2003/0035837 A1 | 2/2003 | Sackler et al. |
| 2003/0044464 A1 | 3/2003 | Ziegler et al. |
| 2003/0054032 A1 | 3/2003 | Oshlack et al. |
| 2003/0068371 A1 | 4/2003 | Oshlack et al. |
| 2003/0068375 A1 | 4/2003 | Wright et al. |
| 2003/0069314 A1 | 4/2003 | Christoph et al. |
| 2003/0092724 A1 | 5/2003 | Kao et al. |
| 2003/0104061 A1 | 6/2003 | Bartholomaeus et al. |
| 2003/0143270 A1 | 7/2003 | Deboeck et al. |
| 2003/0148992 A1 | 8/2003 | Block et al. |
| 2003/0152627 A1 | 8/2003 | Beckert et al. |
| 2003/0158242 A1 | 8/2003 | Kugelmann |
| 2003/0180362 A1 * | 9/2003 | Park et al. ............... 424/470 |
| 2004/0131671 A1 | 7/2004 | Zhang et al. |
| 2004/0136924 A1 | 7/2004 | Boyd et al. |
| 2004/0185096 A1 | 9/2004 | Oshlack et al. |
| 2004/0202716 A1 | 10/2004 | Chan et al. |
| 2004/0259956 A1 | 12/2004 | Wright et al. |
| 2005/0003002 A1 | 1/2005 | Ziegler et al. |
| 2005/0157382 A1 | 7/2005 | Kafka et al. |
| 2005/0256131 A1 | 11/2005 | Coester |
| 2005/0276852 A1 | 12/2005 | Davis et al. |
| 2006/0009465 A1 * | 1/2006 | Edgar et al. ............. 514/253.04 |
| 2006/0111307 A1 | 5/2006 | Robbins |
| 2006/0115530 A1 | 6/2006 | Pettersson et al. |
| 2006/0172006 A1 | 8/2006 | Lenaerts et al. |
| 2006/0193911 A1 | 8/2006 | Ketsela et al. |
| 2006/0240107 A1 | 10/2006 | Lenaerts et al. |
| 2006/0269603 A1 | 11/2006 | Brown Miller et al. |
| 2007/0003618 A1 | 1/2007 | Lenaerts et al. |
| 2007/0048376 A1 | 3/2007 | Baichwal et al. |
| 2007/0128269 A1 | 6/2007 | Gervais et al. |
| 2007/0237816 A1 | 10/2007 | Finkelstein |
| 2008/0096872 A1 * | 4/2008 | Friedman ............... 514/220 |
| 2009/0047345 A9 | 2/2009 | Lenaerts et al. |
| 2009/0238870 A1 | 9/2009 | Fonknechten et al. |

(56) References Cited

U.S. PATENT DOCUMENTS

| | | |
|---|---|---|
| 2011/0015205 A1 | 1/2011 | Gervais et al. |
| 2011/0027370 A1 | 2/2011 | Gervais et al. |
| 2011/0033537 A1 | 2/2011 | Gervais et al. |

FOREIGN PATENT DOCUMENTS

| | | |
|---|---|---|
| CA | 2 280 534 | 8/1998 |
| CA | 2 321 461 | 9/1999 |
| CA | 2295469 | 7/2000 |
| CA | 2 414 349 | 1/2002 |
| CA | 2 433 668 | 6/2002 |
| CA | 2 466 032 | 5/2003 |
| CA | 2 503 155 | 5/2004 |
| CA | 2 503 361 | 5/2004 |
| CA | 2 489 855 | 4/2005 |
| CL | 172000 | 10/2000 |
| DE | 4315525 | 11/1994 |
| DE | 4329794 | 3/1995 |
| DE | 19530575 | 2/1997 |
| DE | 19901683 | 7/2000 |
| DE | 19901687 | 7/2000 |
| DE | 19940740.1 | 3/2001 |
| DE | 19940944.7 | 3/2001 |
| DE | 10023699.5 | 4/2001 |
| DE | 19947747 | 4/2001 |
| DE | 19901686 | 6/2006 |
| EP | 299877 A1 | 1/1989 |
| EP | 0 566 709 | 10/1993 |
| EP | 0 624 366 | 11/1994 |
| EP | 0624366 | 11/1994 |
| EP | 0636370 | 2/1995 |
| EP | 0 642 788 | 3/1995 |
| EP | 0654263 | 5/1995 |
| EP | 0699436 | 3/1996 |
| EP | 0 729 751 | 9/1996 |
| EP | 0759296 | 2/1997 |
| EP | 785775 A1 | 7/1997 |
| EP | 0 864 325 | 9/1998 |
| EP | 1020183 | 7/2000 |
| EP | 1020185 | 7/2000 |
| EP | 1020186 | 7/2000 |
| EP | 1 138 320 | 10/2001 |
| EP | 1 190 712 | 3/2002 |
| EP | 1207866 | 5/2002 |
| EP | 1207867 | 5/2002 |
| EP | 1207868 | 5/2002 |
| EP | 1217998 | 7/2002 |
| EP | 1 468 679 | 10/2004 |
| EP | 1 527 775 | 5/2005 |
| EP | 1576986 | 9/2005 |
| EP | 1576986 A2 * | 9/2005 |
| EP | 1627633 | 2/2006 |
| GB | 2284760 | 6/1995 |
| JP | 10-095801 | 4/1998 |
| WO | WO 94/02121 | 2/1994 |
| WO | WO-98/40053 | 9/1998 |
| WO | WO-99/01111 | 1/1999 |
| WO | WO-00/25769 | 5/2000 |
| WO | WO-00/32558 | 6/2000 |
| WO | WO-0041681 | 7/2000 |
| WO | WO-01/15667 | 3/2001 |
| WO | WO-01/15683 | 3/2001 |
| WO | WO-0115681 | 3/2001 |
| WO | WO-0115682 | 3/2001 |
| WO | WO-01/24783 | 4/2001 |
| WO | WO-01/45676 | 6/2001 |
| WO | WO-02/02084 A1 | 1/2002 |
| WO | WO-02/43706 | 6/2002 |
| WO | WO-02/060415 | 8/2002 |
| WO | WO-03/037296 | 5/2003 |
| WO | WO 03037296 A2 * | 5/2003 |
| WO | WO-03/072025 | 9/2003 |
| WO | WO-03/080031 | 10/2003 |
| WO | WO-03099265 | 12/2003 |
| WO | WO-2004003722 | 1/2004 |
| WO | WO-2004/037222 | 5/2004 |
| WO | WO 2004038428 A2 * | 5/2004 |
| WO | WO-2004/080447 | 9/2004 |
| WO | WO-2010019279 | 2/2010 |

OTHER PUBLICATIONS

Fabre, "Trazodone Dosing Regimen: Experience with Single Daily Administration," J. Clin. Psychiatry 51:9 (suppl.), pp. 23-26 (1990).
Haria et al., "Trazodone: A Review of its Pharmacology, Therapeutic Use in Depression and Therapeutic Potential in Other Disorders," Drugs & Aging 4(4):331-355 (1994).
Kasper et al., "A Comparative, Randomised, Double-Blind Study of Trazodone Prolonged-Release and Paroxetine in the Treatment of Patients with Major Depressive Disorder," Current Med. Res. & Opinion vol. 21 No. 8, pp. 1139-1146 (2005).
Mateescu, "Use of Crosslinked Amylose for the Quantitative Determination of $\alpha$ - and $\beta$-Amylase," Lab. Enzymol., Inst. Sci. Biol., Bucharest, Rom., Biochimie 60(5), 535-7 (1978) (English Abstract provided).
Mendelson, "A Review of the Evidence for the Efficacy and Safety of Trazodone in Insomnia," J. Clin. Psychiatry 66:4, pp. 469-476 (2005).
Moon et al., "Efficacy and Tolerability of Controlled-Release Trazodone in Depression: A Large Multi-Centre Study in General Practice," Current Med. Res. and Opinion vol. 12, No. 3, pp. 160-168 (1990).
Saletu-Zyhlarz et al., "Confirmation of the Neurophysiologically Predicted Therapeutic Effects of Trazodone on Its Target Symptoms Depression, Anxiety and Insomnia by Postmarketing Clinical Studies with a Controlled-Release Formulation in Depressed Outpatients," Neuropsychobiology 2003; 48:194-208.
Search Report and Written Opinion for Intl. Application PCT/CA2006/001483, Jun. 4, 2007.
Search Report and Written Opinion for Intl. Application PCT/CA2006/001484, Jun. 8, 2007.
Adler, L. et al., "A Comparison of Once-Daily Tramadol with Normal Release Tramadol in the Treatment of Pain in Osteoarthritis," The Journal of Rheumatology 2002, vol. 29, No. 10, pp. 2196-2199.
Bodalia et al., "A Comparison of the Pharmacokinetics, Clinical Efficacy, and Tolerability of Once-Daily Tramadol Tablets with Normal Release Tramadol Capsules," Journal of Pain and Symptom Management , vol. 25, No. 2, pp. 142-149 (2003).
Boureau, "Tramadol in Post-Herpetic Neuralgia: A Randomized, Double-Blind, Placebo-Controlled Trial," Pain, Elsevier Sci Pub. 2003, vol. 104 (1/2):323-331.
Desmeules, "The tramadol option," European Journal of Pain, 4, Suppl. A:15-21 (2000).
Fleischmann, "Tramadol for the treatment of joint pain associated with osteoarthritis: a randomized, double-blind, placebo-controlled trial," Current Therapeutic Research 62(2):113-128 (2001).
International Search Report for International Patent Application No. PCT/CA03/01637, dated Apr. 27, 2004.
International Search Report for International Patent Application No. PCT/CA03/01638, dated Apr. 27, 2004.
Klaschik, "Office-oriented pain therapy in cancer patients—Adequate alleviation of pain with the appropriate medication," Klinikarzt 31(9):250-256 (2002). (English abstract provided on p. 256).
Partial European Search Report for EP 04 02 4164, Aug. 9, 2006.
Ruoff, "Slowing the initial titration rate of tramadol improves tolerability," Pharmacotherapy 19(1):88-93 (Jan. 1999).
Stamer, "Impact of CYP2D6 genotype on postoperative tramadol analgesia," Pain, 105(1-2):231-238 (2003).
Visavarungroj, N. et al., "Crosslinked Starch as a Disintegrating Agent," International Journal of Pharmaceutics 1990, vol. 62, No. 2/3, pp. 125-131.
De Jong (1997) "Comment on the hypoalgesic effect of tramadol in relation to CYP2D6," Pain Dig. 7:245.
Kogel et al., "Involvement of metabolites in the analgesic action of tramadol," Proc. 9th World Congress on Pain, Vienna, Austria, Aug. 22-27, 1999, pp. 523.

(56) References Cited

OTHER PUBLICATIONS

Opposition statement against Chilean Application No. 2186-2003 by La Asociacion Industrial De Laboratorios Farmaceuticos A.G. (in Spanish) and its English translation.
Opposition statement against Chilean Application No. 2187-2003 by La Asociacion Industrial De Laboratorios Farmaceuticos A.G. (in Spanish) and its English translation.
Opposition statement against Chilean Application No. 2187-2003 by Laboratorios Recalcine S.A. (in Spanish) and its English translation.
Roth (1998) "Efficacy and safety of tramadol HCL in breakthrough musculoskeletal pain attributed to osteoarthritis," J. Rheumatol 25:1358-63.
Ruoff (1999) "Strategies to Control Chronic Musculoskeletal Pain: A Guide to Drug Therapy," Consultant, 39:2773-81.
Wilder-Smith et al. (2001) "Treatment of severe pain from osteoarthritis with slow-release tramadol or dihydrocodeine in combination with NSAID's: a randomized study comparing analgesia, antinociception and gastrointestinal effects," Pain 91:23-31.
Excerpt from "Handbook of Pharmaceutical Controlled Release Technology," Donald L. Wise, Executive Editor (2000) (80 pages).
Excerpt from "Controlled Drug Delivery. Fundamentals and Applications," Second Edition, Revised and Expanded, Joseph R. Robinson, et al., Editors (1987) (68 pages).
Opposition statement against Chilean Application No. 600-2007 by Asociacion Industrial de Laboratorios Farmaceuticos AG (in Spanish) and an English translation.
Opposition statement against Chilean Application No. 605-2007 by Laboratorios Recalcine S.A. (in Spanish) and an English translation.
Gennaro R. Alfonso, Remington Farmacia, 19th Edition, Panamericana, Spain. 1988, pp. 2470, 2535 (in Spanish) and an English translation.
Nies and Spielberg, Goodman & Gilman. Las Bases Farmacologicas de la Terapeutica. Novena Edicion. vol. I. McGraw-Hill. Interamericana. Mexico. 1996, pp. 47, 58 (in Spanish) and an English translation.
Opposition statement against Chilean Application No. 605-2007 by Asociacion Industrial de Laboratorios Farmaceuticos AG (in Spanish) and an English translation.
Labopharm, Inc. Press Release dated Feb. 2, 2010 relating to FDA approval of OLEPTRO™ (4 pages).
Labopharm, Inc. Press Release dated Nov. 12, 2010 relating to ANDA Submission with Paragraph IV Certification for Generic of OLEPTRO™ (2 pages).
Lenaerts et al. (1998) "Cross-linked high amylose starch for controlled release of drugs: recent advances" Journal of Controlled Release 53:225-234.
Ispas-Szabo et al. (1999) "Structure-properties relationship in cross-linked high-amylose starch for use in controlled drug release" Carbohydrate Research. Pergamon. 323:163-175.
Lenaerts et al. (1991) "Controlled release of 1-42 theophylline from cross-linked amylose tablets" Journal of Controlled Release 15:39-46.
Supplementary European Search Report for EP 06 79 0660, dated Jun. 24, 2011 (5 pages).
Rotzinger et al. (1998) "Trazodone is Metabolized to $m$-Chlorophenylpiperazine by CYP3A4 From Human Sources" Drug Metabolism and Disposition 26:572-575.
Uncertified translation of Japanese Patent Office Action issued on Apr. 23, 2012 for 2008-529430, which notes JP patent documents identified as B75 and B76 (2 pages).

* cited by examiner

TRAZODONE COMPOSITION FOR ONCE A DAY ADMINISTRATION

RELATED APPLICATIONS

This application is a continuation of U.S. patent application Ser. No. 11/519,194, filed Sep. 11, 2006, which claims the benefit of U.S. Provisional Patent Application Ser. No. 60/715,162, filed Sep. 9, 2005, the entire disclosures of each of which are incorporated by reference herein.

FIELD OF THE INVENTION

The present invention relates to the anti-depressant trazodone and in particular to a once a day formulation of trazodone, and to its use for treating depression and certain sleep disorders.

BACKGROUND

Trazodone is a serotonin-2 receptor antagonist/reuptake inhibitor that also decreases extracellular gamma-aminobutyric acid (GABA) levels in the cerebral cortex, through the blockade of 5-hydroxytryptamine$_{2A}$ (5-HT$_{2A}$) receptors. This decrease is accompanied by an increase in (5-HT) release. Higher doses of trazodone inhibit 5-HT transport and this uptake inhibition results in a further increase in 5-HT levels. It is contemplated that this double mechanism may be responsible for the anti-depressant properties of trazodone. Moreover, the interaction between the GABAergic and serotoninergic systems may explain its sedative, anxiolytic properties.

Trazodone is therefore a psychoactive compound with sedative and anti-depressant properties. It is rapidly absorbed from the upper gastro-intestinal tract and is extensively metabolized after oral administration. It is normally used to relieve symptoms of depression such as feelings of sadness, worthlessness, or guilt; loss of interest in daily activities; changes in appetite; tiredness; thoughts of death or suicide; and insomnia. Trazodone may also be used for other purposes, and details thereof are well documented in the art.

Trazodone is a triazolopyridine derivative of the formula

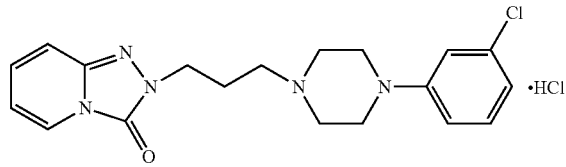 [SMILES: O=c1n(CCCN2CCN(c3cccc(Cl)c3)CC2)nc2ccccn12 ; Cl]

which is shown in its normally used hydrochloride form. Preparation of this compound was first disclosed in U.S. Pat. No. 3,381,009 which issued in 1968 to G. Palazzo et al.

The solubility of trazodone is pH dependent and has a pKa of 6.74 in water. As a result, trazodone is highly soluble in acid media (as found in the stomach and upper intestines) i.e., when below its pKa. In contrast, when above its pKa, its solubility is very low, for example, in the neutral and basic conditions of the lower intestine. Such insolubility obviously has an effect on its dissolution and, therefore, on the availability of the drug for absorption in the lower intestine. These features would be expected to hinder the development of long acting (for example, greater than 8 hours) forms of trazodone, which require substantially uniform absorption along the length of the gastrointestinal tract, in particular, absorption during passage through both the upper and lower intestinal tracts.

As with many drugs, trazodone is normally prescribed as an immediate release form for use two times (BID) or three times (TID) a day, with all the inconveniences and disadvantages that this involves. For example, BID or TID dosing with immediate release forms of trazodone results in concentrations of the drug in the blood that do not remain within the so-called therapeutic window and which, therefore, can be associated with higher risks of dose related adverse effects when reaching high levels, or lower degree of efficacy when reaching low levels. In addition, multiple daily doses may lead to several periods of drowsiness throughout the day associated with peak trazodone concentrations occurring immediately after administration.

As a result, there is a need for a once a day (OAD) formulation of trazodone that from a single tablet rapidly achieves and maintains stable, effective concentrations over 24 hours and more and that is pH-independent in its release profile so that trazodone may be uniformly absorbed along substantially the entirety of the upper and lower gastrointestinal tract, thereby reducing the frequency and severity of side effects such as drowsiness during the day.

SUMMARY OF THE INVENTION

The invention provides a sustained release pharmaceutical composition for once a day oral administration or trazodone or a derivative thereof. The composition comprises from about 15% to about 60% by weight trazodone or a derivative thereof, and from about 15% to about 85% by weight percent of a controlled release excipient. The controlled release excipient, when orally administered to a mammal, for example, a person, permits the trazodone or derivative thereof to achieve an effective plasma concentration from at least about 1 hour to about 24 hours after initial administration. Under certain circumstances, the controlled release excipient provides a substantially pH independent controlled release of the trazodone or derivative thereof so that the trazodone or the trazodone derivative can be absorbed during passage through both the upper and lower gastrointestinal tracts.

The sustained release formulations provide plasma concentrations of trazodone or trazodone derivatives for at least 24 hours that are effective at treating, i.e., ameliorating, one or more of the symptoms of depression. In another embodiment, the sustained release formulations provide effective amounts of trazodone or a trazodone derivative for treating sleeping disorders, for example, improving sleep architecture.

The sustained release excipient can provide a therapeutically effective plasma trazodone or trazodone derivative concentration that remains substantially constant between about 50 ng/mL and about 3000 ng/mL for a period that extends about one hour after ingestion to at least about 24 hours. Plasma concentrations typically are dependent on the dose administered. For example, in one embodiment, a sustained release pharmaceutical composition contemplated herein comprises 150 mg of trazodone hydrochloride. Such a formulation provides an effective plasma trazodone concentration from at least about 1 hour to about 24 hours after initial administration of between about 150 ng/mL and about 500 ng/mL. In another embodiment, the sustained release pharmaceutical composition comprises 300 mg of trazodone hydrochloride. Such a formulation provides an effective plasma trazodone concentration from at least about 1 hour to about 24 hours after initial administration of between about 300 ng/mL and about 1000 ng/mL.

In certain embodiments, the sustained release pharmaceutical composition comprises from about 15% to about 60% by weight trazodone or a derivative thereof and from about 15% to about 85% by weight percent of controlled release excipient. In other embodiments, the composition comprises from about 20% to about 50% weight percent trazodone and from about 20% to about 50% weight percent of controlled release excipient. For example, the composition may comprise about 35% to about 50% weight percent trazodone and from about 15% to about 50% weight percent of controlled release excipient.

It is contemplated that a number of different excipients may be useful in the practice of the invention. In one embodiment, the controlled release excipient comprises cross-linked high amylose starch. In certain embodiments, the cross-linked high amylose starch is cross linked with phosphorus oxychloride and/or comprises hydroxypropyl side chains. In certain embodiments, the cross-linked high amylose starch comprises between about 65% and 75% by weight amylose and is cross-linked with phosphorus oxychloride. One preferred cross-linked high amylose starch useful in the practice of the invention is known as CONTRAMID® cross-linked, high amylose starch, available commercially from Labopharm, Inc., Laval, Canada.

In addition, the sustained release pharmaceutical composition may optionally include more or more pharmaceutical additives. Exemplary pharmaceutical additives include binding agents (for example, hydroxypropylmethylcellulose), solubilizing agents (for example, povidone or cetylpyridinium chloride), acidifying agents (for example, alginic acid), pore forming agents (for example, sucrose), lubricants (for example, sodium stearyl fumarate), and glidants (for example, colloidal silicon dioxide).

In one embodiment, the invention provides a sustained release pharmaceutical composition comprising about 20% to about 50% by weight trazodone hydrochloride, about 20% to about 50% by weight cross-linked high amylose starch, about 10% to about 20% by weight hydroxypropylmethylcellulose, about 0% to about 5% by weight cetylpyridinium chloride, about 0% to about 20% by weight alginic acid, about 1% to about 5% by weight percent sodium stearyl fumarate, and up to about 1% by weight percent colloidal silicon dioxide.

The sustained release pharmaceutical composition can be formulated into a variety of shapes and forms such as tablets and caplets suitable for oral administration. In one embodiment, the invention provides a caplet comprising 300 mg of trazodone. Such a caplet can be adapted for administration before bedtime. Such a formulation rapidly induces somnolence after oral administration but yet provides substantially no drowsiness in a patient about 8 hours after oral administration as compared to repeat administration of an immediate release trazodone composition.

The invention provides for unit dose sustained release pharmaceutical composition for once a day oral administration of 300 mg trazodone hydrochloride is comprising about 20% to about 40% by weight of a controlled release excipient, wherein when ingested orally, the composition provides area under the concentration-time curve substantially equivalent to the commercially available daily dose of three 100 mg strength trazodone hydrochloride tablets, wherein the three tablets are administered over 24 hours. Also provided herein is a unit dose sustained release pharmaceutical composition for once a day oral administration of 150 mg trazodone hydrochloride comprising about 30% to about 50% by weight of a controlled release excipient, wherein when ingested orally, the composition provides area under the concentration-time curve substantially equivalent to the commercially available daily dose of three, 50 mg strength trazodone hydrochloride tablets, wherein the three tablets are administered over 24 hours.

In addition, the invention provides a method of treating depression by administering once a day to a person in need of an anti-depressant, one of the sustained release pharmaceutical compositions described above. The composition can be administered before bedtime.

In addition, the invention provides a method of improving the sleep architecture in a person in need of treatment thereof, the method comprises administering once a day to such a person, one of the sustained release pharmaceutical compositions described above. The composition preferably is administered before bedtime.

BRIEF DESCRIPTION OF THE DRAWINGS

The invention is illustrated but is not limited by the annexed drawings, in which.

DETAILED DESCRIPTION

Figure 1:
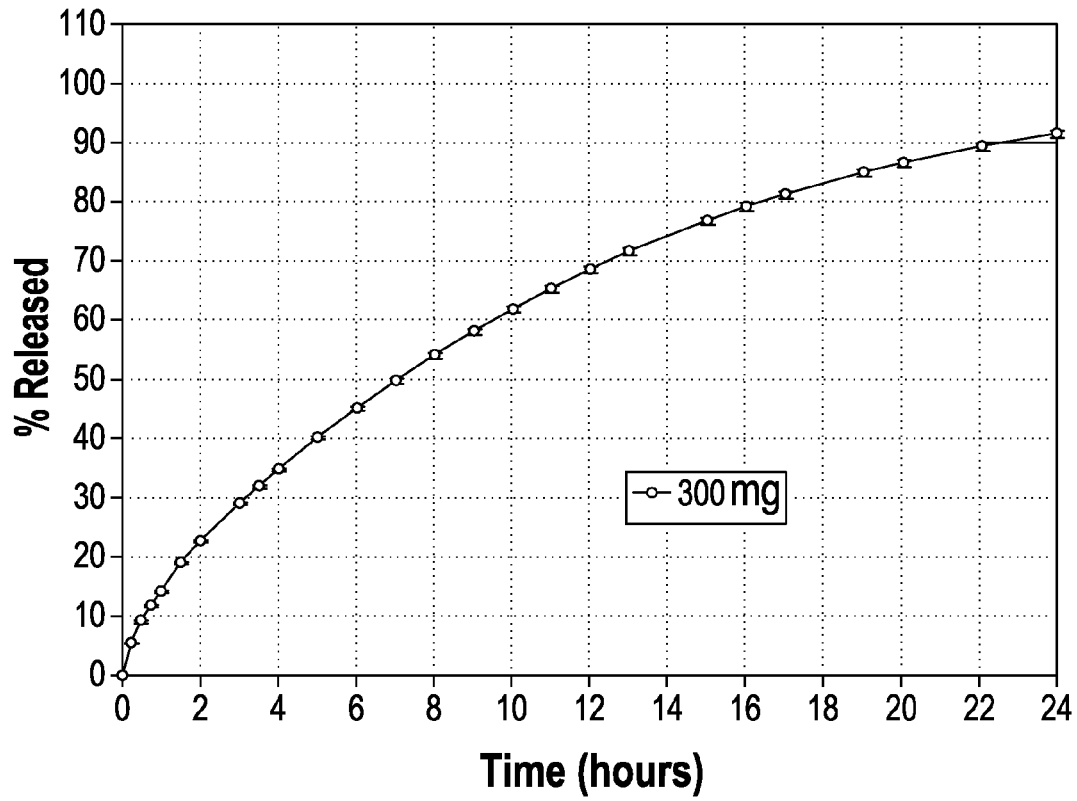
FIG. 1 is a graph illustrating the in vitro dissolution profile of a first 300 mg trazodone OAD formulation.

The invention is based, in part, upon the discovery that it is possible to formulate a once a day formulation of trazodone or a trazodone derivative that provides a plasma concentration of the active ingredient that is essentially stable between one hour and twenty four hours that is effective in the treatment of, i.e., ameliorating one or more of the systems of depression. This discovery was surprising because, even though the solubility of trazodone is pH dependent, and decreases rapidly at the higher pH found in the lower gastrointestinal tract, it has been found that it is possible to provide therapeutic, stable and/or effective concentrations of trazodone in the blood stream for at least 24 hours irrespective of changes in pH through the upper and lower intestinal tracts.

Accordingly, the invention provides a sustained release pharmaceutical composition for once a day oral administration or trazodone or a derivative thereof. The composition comprises from about 15% to about 60% by weight trazodone or a derivative thereof, and from about 15% to about 85% by weight percent of a controlled release excipient. The controlled release excipient, when orally administered to a mammal, for example, a person, permits the trazodone or derivative thereof to achieve and/or maintain an effective plasma concentration, for example, a therapeutically effective plasma concentration from at least about 1 hour to about 24 hours after initial administration for treating depression.

In addition, it is possible to use the same or similar formulations for treating sleep disorders, for example, improving sleep architecture. The controlled release excipient, when orally administered to a mammal, for example, a person, permits the trazodone or derivative thereof to achieve an effective plasma concentration for treating a sleep disorder. Such a formulation rapidly (for example, within 1 hour) induces somnolence after oral administration but yet provides substantially no drowsiness in a patient about 8 hours after oral administration, as compared to repeat administration of an immediate release trazodone composition.

The formulations described herein provide a rapid rise in plasma concentrations of the active ingredient, which thereafter remain relatively and substantially stable for at least 24 hours or more. The plasma concentration between 1 hour and 24 hours remains within about 45% of the mean plasma concentration, more preferably between about 30% of the mean plasma concentration, and most preferably between about 15% of the mean plasma concentration. In certain formulations, after an initial rapid release of trazodone or the trazodone derivative within an hour of ingestion the trazodone or the trazodone derivative is released in vivo with approximately zero order kinetics for at least about 24 hours, leading to plateau plasma concentrations. In these formulations, the effective plasma concentration of the trazodone formulation remains generally constant about 1 hour after ingestion, and can be between about 60 ng/mL and about 3000 ng/mL, between about 150 ng/mL and 1500 ng/mL, between about 600 ng/mL and 1300 ng/mL, between about 500 ng/mL and 1200 ng/mL, or between about 300 ng/mL and 650 ng/mL at least up to about 24 hours after oral administration.

Formulations contemplated herein may reach steady-state, for example, on-average, within a normal population, after about the fourth administration. The peak-to-trough ratio produced by such formulations at steady-state may be about 60% to about 100%.

The sustained release trazodone formulations contemplated herein may have effective plasma concentrations that are for example bioequivalent with respect to the AUC (area under the curve) of a immediate release formulation that is administered, for example, two or three times day. The AUC is a mathematical calculation to evaluate the body's total exposure over time to a given drug and refers to the area under the curve in a plot of concentration of drug against time. AUC's are used as a guide for dosing schedules and to compare the bioavailability of different drug formulations in the body.

The formulations described herein are particularly useful in the delivery of trazodone and trazodone derivatives. Derivatives include pharmaceutically acceptable prodrugs, metabolites, salts and esters, or the like of trazodone. For example, the term "pharmaceutically-acceptable salts" is art-recognized and refers to the relatively non-toxic, inorganic and organic acid addition salts of compounds, including, for example, those contained in compositions of the present invention. In a preferred embodiment, the active ingredient in the formulation is trazodone hydrochloride.

A composition according to the invention may include trazodone or its derivatives and a controlled release excipient. In some embodiments, compositions disclosed herein include more than about 15% trazodone or its derivatives by weight, for example between about 15% and about 60%, or between about 20% and about 60%, or between about 20% and about 55% by weight. In other embodiments, compositions contemplated herein may include more than about 15% weight controlled release excipient, for example, between about, 15% and about 85%, or about 20% and about 85%, or about 20% and about 60%, or about 20% and about 50%, or about 30% to about 50% by weight. The composition according to the invention preferably comprises from about 20% to about 50% by weight, more preferably from about 25% to about 50% trazodone or trazodone derivative, and from about 20% to 50% by weight, more preferably from about 25% to about 50% by weight of controlled release excipient. In a particular embodiment, this invention is directed to a composition comprising about 25% to about 50% trazodone hydrochloride by weight and about 30% to about 50% cross-linked high amylose starch, such as disclosed herein.

A practical example of a sustained release pharmaceutical composition according to the invention, is one containing 150 mg of trazodone hydrochloride. This formulation can provide an effective plasma concentration preferably in the range of about 150 ng/mL to 500 ng/mL between about 1 and 24 hours after the first administration. Another practical example is one wherein the composition comprises 300 mg of trazodone hydrochloride. This formulation can provide a plasma trazodone concentration preferably in the range of about 300 ng/mL to 1000 ng/mL. Of course, other compositions according to the invention may be prepared with different amounts of trazodone or its derivatives with correspondingly varying plasma concentrations that can be for example, between about 50 ng/mL and about 3000 ng/mL.

Controlled release excipients contemplated herein may vary to a large extent as is well known to one skilled in the art, provided that a formulation including an excipient has the disclosed therapeutic action and/or provides a pH independent delivery of trazodone or a trazodone derivative. Controlled release excipients may include cross-linked starches, hydrogels, celluloses, and/or polymers, and other controlled release excipients known to those skilled in the art.

In one embodiment, the controlled release excipient preferably comprises a cross-linked high amylose starch, for example, where the cross-linked high amylose starch is cross-linked with phosphorus oxychloride and/or comprises hydroxypropyl side chains. In certain embodiments, the cross-linked high amylose starch comprises between about 65% and 75% by weight amylose and is cross-linked with phosphorus oxychloride. A suitable excipient has been developed by and is available commercially from Labopharm, Inc., Laval, Canada, under the trademark CONTRAMID®. The synthesis of the CONTRAMID® excipient is described, for example, in U.S. Pat. No. 6,607,748, hereby incorporated by reference in its entirety for all purposes. Compositions contemplated herein may include cross-linked high amylose starch together with one or more additional controlled release excipients.

Cross-linking of starch represents a powerful method for modifying starch. Usually, starch granules are cross-linked to increase resistance of the paste to shear or heat. Such chemically cross-linked starches provide a desirable smooth texture and possess viscosity stability throughout processing operations and normal shelf life. In some embodiments, cross-linked high amylose starch as contemplated herein may be gelatinized after cross-linking. In a preferred embodiment, cross-linking high amylose starch may include additional chemical modification (e.g., hydroxypropylation) prior to gelatinization.

The cross-linking of high amylose starch may be realized according to procedures described in the art. For example, cross-linking of amylose can be carried out in the manner described in Mateescu [BIOCHEMIE 60: 535-537 (1978)] by reacting amylose with epichlorohydrin in an alkaline medium. In the same manner, starch can also be cross-linked with a reagent selected from the group consisting of epichlorohydrin, adipic acid anhydride, sodium trimetaphosphate and phosphorous oxychloride or other cross-linking agents including, but not limited to, 2,3-dibromopropanol, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis (hydroxymethyl) ethyleneurea, mixed carbonic-carboxylic acid anhydrides, imidazolides of carbonic and polybasic carboxylic acids, imidazolium salts of polybasic carboxylic acids, and guanidine derivatives of polycarboxylic acids. The reaction conditions employed will vary with the type and amount of the cross-linking agent that is used, as well as the base concentration, amount and type of starch.

It is contemplated that starches containing more than about 40% w/w amylose can be used to form cross-linked high amylose starch, e.g., pea and wrinkled pea starch, bean starch, hybrids or genetically modified tapioca or potato starch, or any other root, tuber or cereal starch. Preferably, high amylose starch containing about 70% w/w amylose is used as the base material. For example, high amylose starch, Cerestar AmyloGel 03003 (Cerestar U.S.A. Inc.), may be used.

It has been discovered that by combining trazodone or a trazodone derivative with a controlled release excipient, for example, cross-linked high amylase starch (for example, CONTRAMID® cross-linked high amylose starch), trazodone, which is pH sensitive with a pKa of about 6.74 can be released and absorbed not only in the upper gastrointestinal tract where the pH is below the pKa of trazodone (where trazodone is soluble) but also in the lower gastrointestinal tract where the pH is above the pKa of trazodone (where trazodone is poorly soluble) thereby maintaining stable plasma concentrations in the blood throughout gastrointestinal transit. To this day, to our knowledge, no once a day formulation including a pH dependent active agent has been suggested or designed for a composition that has the pharmacokinetic profile described herein.

The pharmaceutical composition according to the invention may also comprise pharmaceutically acceptable additives. Such additives can include, for example, sugars, such as lactose, glucose and sucrose; other starches, such as corn starch and potato starch; cellulose, and its derivatives, such as sodium carboxymethyl cellulose, ethyl cellulose and cellulose acetate; powdered tragacanth; malt; gelatin; talc; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; and other non-toxic compatible substances employed in pharmaceutical formulations. Such additives may also include colorants.

For example, the compositions disclosed herein may include any one of a mixture of a binding agent, a solubilizing agent, an acidifying agent, a pore forming agent, a lubricant, a glidant, and the like, as is well known to those skilled in the art. Preferred pharmaceutical additives that are used in providing a composition according to the invention may include, for example, binding agents that include, for example, hydroxypropylmethylcellulose, hydroxypropylcellulose, hydroxyethylcellulose, methylcellulose, dicalcium phosphate, calcium phosphate, microcrystalline cellulose, or the like, solubilizing agents that include, for example, povidone, cetylpyridinium chloride, or the like, acidifying agents that include, for example, alginic acid, citric acid, succinic acid, bile acid or the like, pore forming agents, that include, for example, sucrose, lactose, mannitol or the like, lubricants that include, for example, sodium stearyl fumarate, magnesium stearate, calcium stearate, stearic acid, hydrogentated vegetable oils or the like and/or glidants that include, for example, colloidal silicon dioxide, talc or the like. Other additives that are well known to those skilled in the art may of course be included in the composition according to the invention without departing from the scope and spirit of the present invention.

For example, the composition according to the invention may comprise about 20 to 50 weight percent trazodone hydrochloride, about 20 to 50 weight percent cross-linked high amylase starch (for example, CONTRAMID® cross-linked high amylose starch), about 10 to 25 weight percent hydroxypropylmethylcellulose, about 0 to 10 weight percent cetylpyridinium chloride, about 0 to 20 weight percent alginic acid, about 1 to 5 weight percent sodium stearyl fumarate, and up to about 1 weight percent colloidal silicon dioxide.

The composition according to the invention is normally prepared in the form of a tablet. Although the tablet can adopt a wide variety of shapes as is well known to those skilled in the art, the preferred shape is a caplet. Such caplets may be formed using, for example, upper and lower punches as is known in the art. In some embodiments, tablets may include a coat, such as, for example, a coating with a colorant. Suitable coatings include, for example, aqueous film coating polymers such as polyvinyl alcohol, talc, macrogol and the like, and mixtures thereof. Suitable colorants include, for example, iron oxides, lakes, natural colorants and other colorants known to those skilled in the art.

In an exemplary formulation protocol for producing a 5 kg batch of an exemplary sustained release formulation, CONTRAMID® excipient, hydroxypropylmethyl cellulose, trazodone HCl and sodium stearyl fumarate are individually weighed and sifted through a 30 mesh filter. Colloidal silicon dioxide is weighed and pre-blended with CONTRAMID®, sifted through a 30 mesh filter, and blended for 10-30 seconds, for example, 15 seconds to produce a pre-blend. Hydroxypropylmethylcellulose, trazodone and the Contramid®-collodial silicon dioxide pre-blend, are combined and blended for 5-10 minutes, for example, 7 minutes, to produce a bulk blend. A small portion of the resulting bulk blend is combined with the sodium stearyl fumarate and blended for 20-60 seconds, for example, 30 seconds. The resulting sodium stearyl fumarate blend is combined with the residual bulk blend, and the resulting mixture blended for about 2-6 minutes, for example, 4 minutes. The final blend is compressed into tablets using a compression pressure of 27 kN. Caplets are formed using a caplet standard concave punch.

A dosage for once a day administration may be 25 mg to 600 mg of trazodone or a trazodone derivative. Typical doses for once a day administration include 150 mg or 300 mg of trazodone or a trazodone derivative, although this amount may vary to a large extent depending on required needs, and the specific requirements of the treating physician. For example, the dosage of any compositions of the present invention will vary depending on the symptoms, age and body weight of the patient, the nature and severity of the disorder to be treated or prevented, the route of administration, and the form of the subject composition. Dosages for the compositions of the present invention may be readily determined by techniques known to those of skill in the art or as taught herein. The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The resulting formulations have in vitro profiles, preferably, as described in Examples 1 and 3, hereinbelow. The in vitro release profiles were measured as follows. Briefly, the release rates were determined using a U.S.P. paddle method (apparatus type II as described in U.S.P. XXVI) at 150 revolutions per minute, at 37±0.5° C., in 900 mL of hydrochloride/sodium chloride pH 1.2 solution (acid stage) followed after one hour by 900 mL of sodium phosphate monobasic buffer pH 6.0 (buffer stage). In some embodiments; formulations may have release kinetics, whereby, when tested by the foregoing method, not more than about 30% of the active ingredient is released by 1 hour after initiation of the experiment, about 35% to 60% of the active ingredient is released by 6 hours, not more than about 80% of the active ingredient is released by 12 hours, and/or not less than about 80% of the active ingredient is released by 24 hours.

The compositions described herein are particularly useful in treating depression, disorders associated with depression, and sleep disorders. According, a mammal suffering from depression can be administered once a day (for example, at bedtime) with a trazodone formulation as defined above. A mammal to be treated by the subject method may mean either a human or non-human animal.

The compositions described herein may also be useful in treating patients that have difficulty sleeping and/or have disrupted sleep architecture, i.e., disrupted non-REM/REM stage and cycle infrastructure of sleep. In some embodiments, formulations disclosed herein release a therapeutically effective portion of trazodone within one hour after oral administration and thus rapidly induce somnolence but yet provide substantially no drowsiness in a patient about 8 hours after oral administration as compared to repeat administration of an immediate release trazodone composition. Accordingly, such formulations reduce undesirable drowsiness in waking hours or in the day time.

The invention will now be illustrated by means of the following examples which are given for the purpose of illustration only and without any intention to limit the scope of the present invention.

EXAMPLES

Example 1

A first sustained release 300 mg trazodone containing formulation (denoted Formulation 1) was prepared having the composition set forth in TABLE 1.

TABLE 1

Formulation 1

| Ingredients | Tablet (mg) | Tablet % |
|---|---|---|
| CONTRAMID ® excipient | 200 | 32.7 |
| Trazodone HCl | 300 | 49.0 |
| Hydroxylpropylmethyl cellulose K100M | 100 | 16.3 |
| Colloidal silicon dioxide | 3 | 0.5 |
| Sodium stearyl fumarate | 9 | 1.5 |
| Total | 612 | 100 |

The in vitro release kinetics of this formulation were measured using the U.S.P. paddle method (apparatus type II as described in U.S.P. XXVI) at 150 revolutions per minute, at 37±0.5° C., in 900 mL of hydrochloride/sodium chloride pH 1.2 solution (acid stage) followed after one hour by 900 mL of sodium phosphate monobasic buffer pH 6.0 (buffer stage). This formulation, when tested using the foregoing method, had an in vitro release profile where not more than about 30% of the active ingredient was released by 1 hour after initiation of the experiment, about 35% to 55% of the active ingredient was released by 6 hours, not more than 80% of the active ingredient was released by 12 hours, and not less than 80% of the active ingredient was released by 24 hours.

Figure 2:
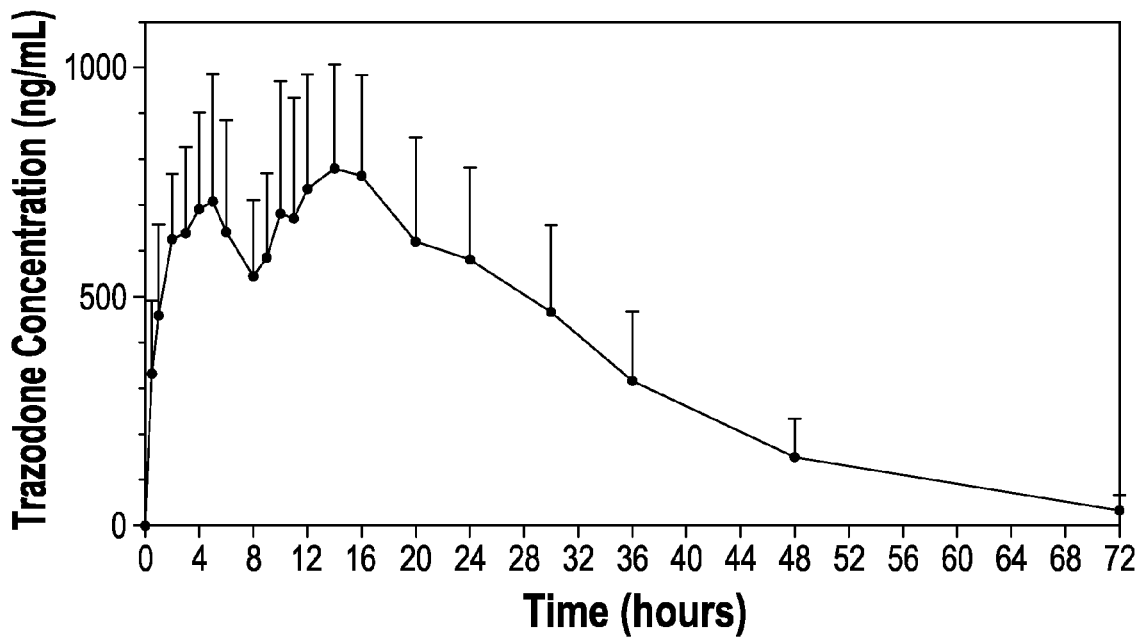
FIG. 2 is graph that illustrates the plasma trazodone concentration derived from a single tablet of the first 300 mg trazodone OAD formulation as a function of time when administered to a human.

In addition, the formulation was tested in vivo. The pharmacokinetics of this formulation were compared with those of the commercial products Trittico® AC 150 mg CR tablets given BID, and Desyrel® 100 mg IR tablets given TID in a human randomized pharmacokinetic crossover study. It was found that following administration of Formulation 1, trazodone plasma concentrations increased more gradually and peak trazodone plasma concentrations were lower than those of either of the reference products. The mean plasma trazodone concentration measured in 18 patients is shown in FIG. 2. The results indicate that this formulation provides a therapeutic plasma concentration within about 1 hour and provides a substantially constant trazodone concentration from 1 hour to 24 hours. The trazodone plasma concentrations at 24 hours were similar to those following TID administration of Desyrel® and BID administration of Trittico® AC.

The in vivo experiments demonstrate that following oral administration of Formulation 1, after a short period to reach acceptable plasma concentrations, trazodone plasma concentrations were maintained at a relatively constant level from approximately 1 hour post-administration to at least 24 hours post-administration.

Example 2

A second sustained release 300 mg trazodone containing formulation (denoted Formulation 2) was prepared having the composition set forth in TABLE 2.

TABLE 2

Formulation 2

| Ingredients | Tablet (mg) | Tablet % |
|---|---|---|
| CONTRAMID ® excipient | 169 | 24.1 |
| Trazodone HCl | 300 | 24.1 |
| Hydroxypropylmethyl cellulose K110M | 105 | 15.0 |
| Alginic acid | 105 | 15.0 |

TABLE 2-continued

Formulation 2

| Ingredients | Tablet (mg) | Tablet % |
|---|---|---|
| Cetylpyridinium chloride | 7 | 1.0 |
| Colloidal silicon dioxide | 3.5 | 0.5 |
| Sodium stearyl fumarate | 10.5 | 1.5 |
| Total | 700 | 10 |

Figure 3:
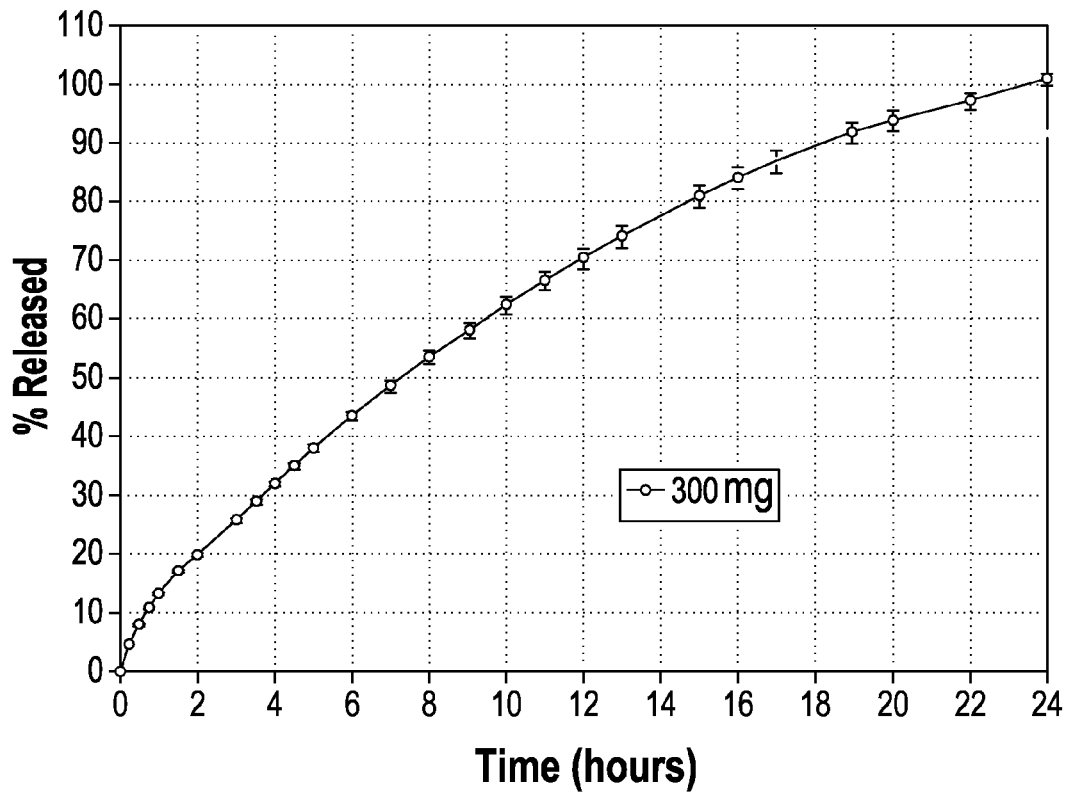
FIG. 3 is a graph illustrating the in vitro dissolution profile of a second 300 mg trazodone OAD formulation.
Figure 4:
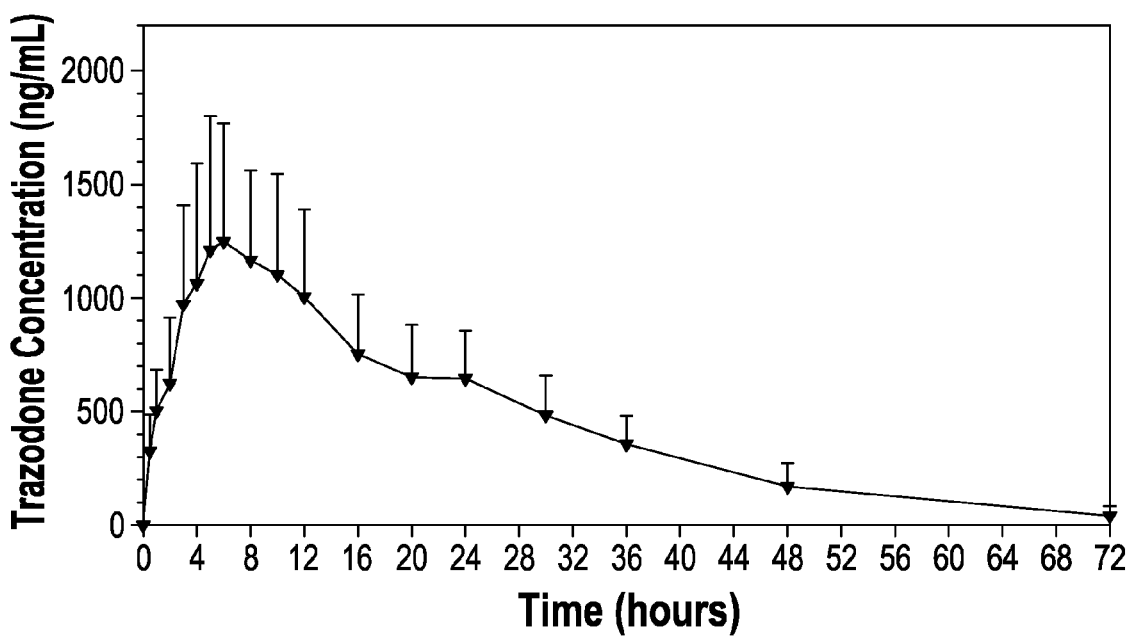
FIG. 4 is graph that illustrates the plasma trazodone concentration derived from a single tablet of a second 300 mg trazodone OAD formulation as a function of time when administered to a human.

The in vitro release kinetics of Formulation 2 were measured using the U.S.P. paddle method as described in Example 1. The in vitro dissolution profile (FIG. 3) shows that in this formulation, not more than about 30% of the active ingredient was released by 1 hour after initiation of the experiment, about 35% to 55% of the active ingredient was released by 6 hours, not more than 80% of the active ingredient was released by 12 hours, and not less than 80% of the active ingredient was released by 24 hours Formulation 2 was also evaluated in vivo. The results obtained were substantially the same when Formulation 2 was compared with Trittico® AC and Desyrel®. The mean plasma trazodone concentration measured in 19 patients is shown in FIG. 4. It was found that following administration of Formulation 2, trazodone plasma concentrations increased to provide a therapeutic concentration in about 1 hour. The plasma concentrations increased till about 6 hours after oral administration but then gradually declined. The plasma concentration of trazodone provided by Formulation 1 was more stable between 1 hours and 24 hours than that provided by Formulation 2.

Example 3

A first sustained release 150 mg trazodone containing formulation (denoted Formulation 3) was prepared having the composition set forth in TABLE 3.

TABLE 3

Formulation 3

| Ingredients | Tablet (mg) | Tablet % |
|---|---|---|
| CONTRAMID ® excipient | 252 | 46.8 |
| Trazodone HCl | 150 | 27.8 |
| Hydroxypropylmethylcellulose K100M | 126 | 23.4 |
| Colloidal silicon dioxide | 3 | 0.5 |
| Sodium stearyl fumarate | 8 | 1.5 |
| Total | 540 | 100 |

Figure 5:
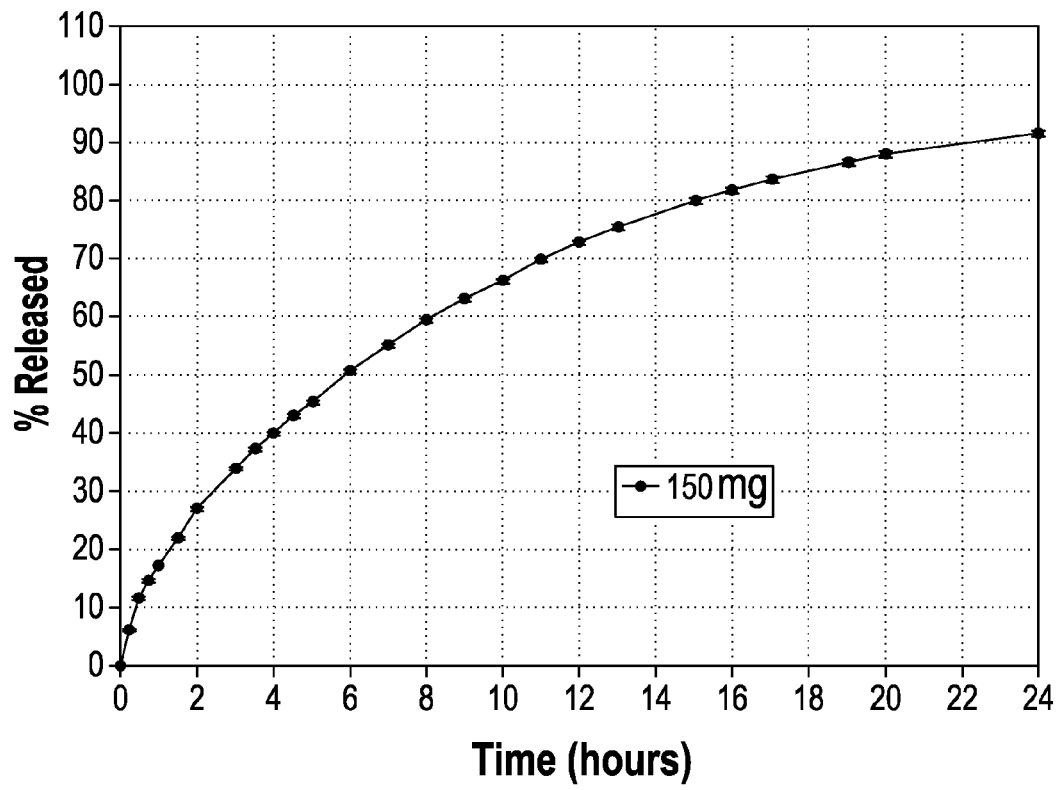
FIG. 5 is a graph illustrating the in vitro dissolution profile of a 150 mg trazodone OAD formulation.

The in vitro release kinetics of Formulation 3 were measured using the U.S.P. paddle method as described in Example 1. The in vitro dissolution profile (FIG. 5) shows that in this formulation, not more than about 30% of the active ingredient was released by 1 hour after initiation of the experiment, about 40% to 60% of the active ingredient was released by 6 hours, not more than 80% of the active ingredient was released by 12 hours, and not less than 80% of the active ingredient was released by 24 hours.

Figure 6:
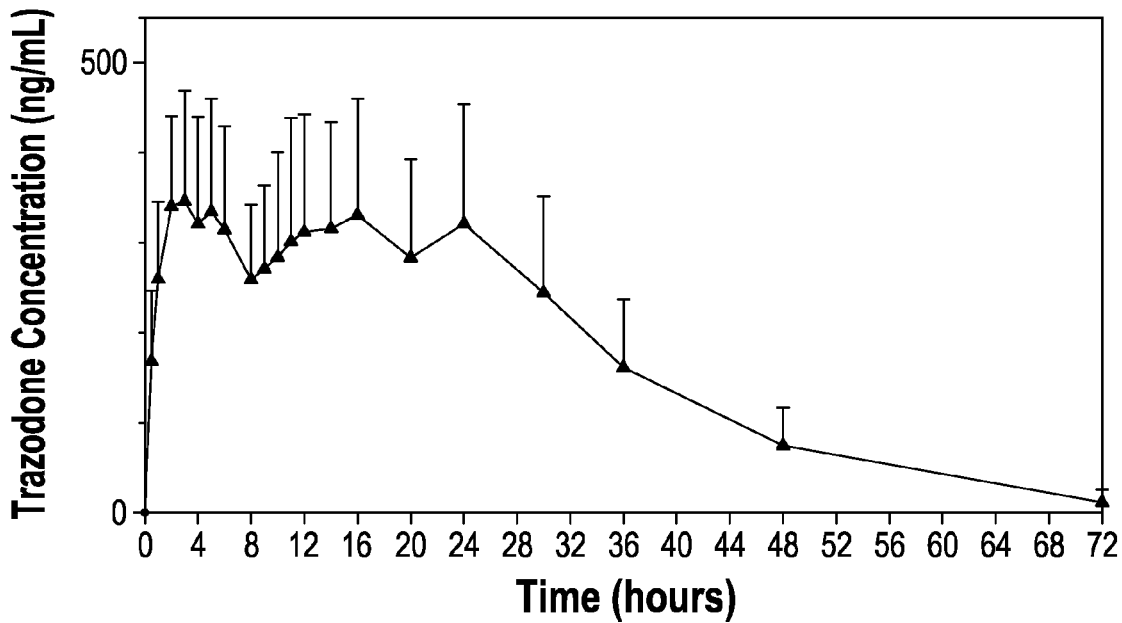
FIG. 6 is graph that illustrates the plasma trazodone concentration derived from a single tablet of a 150 mg trazodone OAD formulation as a function of time when administered to a human.

Formulation 2 was also evaluated in vivo. The mean plasma trazodone concentration measured in 18 patients is shown in FIG. 6. It was found that following administration of Formulation 3, trazodone plasma concentrations increased rapidly to provide a therapeutic concentration in about 1 hour. The results indicate a substantially constant trazodone concentration from 1 hour to 24 hours. As with formulation 1, this appears to show zero order release kinetics between 1 hour and 24 hours following oral administration.

INCORPORATION BY REFERENCE

The entire disclosure of each of the documents referred to herein is incorporated by reference for all purposes.

EQUIVALENTS

Although the present invention has been illustrated by means of preferred embodiments thereof, it is understood that the invention intends to cover broad aspects thereof without departing from the spirit and scope of the invention as defined in the appended claims.

What is claimed is:

1. A method of treating a sleeping disorder in a person in need thereof, the method comprising administering to the person a sustained release pharmaceutical composition consisting essentially of: from about 15% to about 60% by weight trazodone hydrochloride, and from about 15% to about 85% by weight of a hydrogel that provides a substantially pH-independent controlled release of the trazodone hydrochloride, wherein the composition, when administered to the person, permits a pH-independent release of the trazodone hydrochloride so as to maintain a substantially constant effective plasma concentration between about 50 ng/mL and about 3000 ng/mL from at least about one hour to at least about 24 hour after initial administration.

2. The method according to claim 1, wherein the plasma concentration is effective at treating the sleep disorder in the person.

3. The method according to claim 1, wherein the amount of trazodone hydrochloride is 150 mg.

4. The method according to claim 3, wherein the plasma concentration of trazodone hydrochloride achieved one hour after ingestion is between about 150 ng/mL and about 500 ng/mL.

5. The method according to claim 1, wherein the amount of trazodone hydrochloride is 300 mg.

6. The method according to claim 5, wherein the plasma concentration of trazodone hydrochloride achieved one hour after ingestion is between about 300 ng/mL and about 1000 ng/mL.

7. The method according to claim 1, wherein the percent amount of trazodone hydrochloride is from about 20% to about 50% by weight of the composition, and the amount of hydrogel is from about 20% to about 50% by weight of the composition.

8. The method according to claim 7, wherein the percent amount of trazodone hydrochloride is from about 35% to 50% by weight of the composition, and the amount of hydrogel is from about 15% to about 50% by weight of the composition.

9. The method according to claim 1, wherein the hydrogel is a cross-linked high amylose starch.

10. The method according to claim 9, wherein the amount of the cross-linked high amylose starch is between about 65% and 75% by weight amylose and is cross-linked with phosphorus oxychloride.

11. The method according to claim 1, wherein the hydrogel is a cross-linked high amylose starch with hydroxypropyl side chains.

12. The method according to claim 11, wherein the cross-linked high amylose starch is gelatinized.

13. The method according to claim 1, wherein the person is a human.

14. The method according to claim 1, wherein the composition is in the form of a tablet.

15. The method according to claim 1, wherein the composition is in the form of a caplet.

* * * * *